(12) United States Patent
Platzek et al.

(10) Patent No.: US 7,321,044 B2
(45) Date of Patent: Jan. 22, 2008

(54) SYNTHESIS OF OXYGEN-SUBSTITUTED BENZOCYCLOHEPTENES AS VALUABLE INTERMEDIATE PRODUCTS FOR THE PRODUCTION OF TISSUE-SELECTIVE ESTROGENS

(75) Inventors: Johannes Platzek, Berlin (DE); Wolfgang Beckmann, Berlin (DE); Jens Geisler, Berlin (DE); Holger Kirstein, Berlin (DE); Ulrich Niedballa, Berlin (DE); Eckhard Ottow, Berlin (DE); Sigmar Radau, Berlin (DE); Claudia Schulz, Berlin (DE); Thomas Wessa, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 600 days.

(21) Appl. No.: 10/270,080

(22) Filed: Oct. 15, 2002

(65) Prior Publication Data
US 2003/0162974 A1    Aug. 28, 2003

Related U.S. Application Data

(60) Provisional application No. 60/330,681, filed on Oct. 29, 2001.

(30) Foreign Application Priority Data
Oct. 12, 2001    (DE)    ................ 101 51 095

(51) Int. Cl.
C07D 211/70    (2006.01)
C07D 233/56    (2006.01)

(52) U.S. Cl. .................. 546/339; 546/341; 548/346.1; 549/80; 568/319; 568/633; 562/456

(58) Field of Classification Search ................ 562/465, 562/456; 546/339, 341; 548/346, 346.1; 549/80; 568/319, 633
See application file for complete search history.

(56) References Cited

U.S. PATENT DOCUMENTS

| | | | |
|---|---|---|---|
| 3,238,218 A | 3/1966 | Bencze | |
| 6,495,607 B2 * | 12/2002 | Bohlmann et al. | ........... 514/706 |
| 6,878,750 B2 * | 4/2005 | Bohlmann et al. | ........... 514/706 |
| 2002/0068765 A1 | 6/2002 | Bohlmann et al. | |

FOREIGN PATENT DOCUMENTS

| | | |
|---|---|---|
| DE | 198 33 786 A1 | 1/2000 |
| WO | WO86/04904 | 8/1986 |
| WO | WO 00/03979 | * 1/2000 |

OTHER PUBLICATIONS

Sangwan et al, Indian J. Chem. Sect. B, 1986, pp. 832-837.*
Romm et al, Journal of General Chemistry, USSR, (1976) vol. 46, p. 2343-2347.*
Sangman et al, Indian J. Chem. Section B, (1986), pp. 832-837.*
Romm et al, Journal of General Chemistry, USSR, (1976), 46, pp. 2343-2347.*
Sangwan et al (Indian Journal of Chemistry, vol. 25B, Aug. 1986, pp. 832-837.)*
Gapinski et al (J. Med. Chem. 1988, 31, pp. 172-175.)*
Toyama Chemical Co. (Chem Abstract 97:91946 and JP 57014555.*
Nongkhlaw et al (Journal of the Chemical Society, Perkin Transactions May 1, 2001, (11)).*
Nakamura et al (Chemical Abstracts and JP 04161932).*
K.C. Rice, "A Rapid, High-Yield Conversion of Codeine to Morphine," Journal of Medicinal Chemistry, 1977, vol. 20, No. 1, pp. 164-165.
H. Meerwein, "Methoden zur Herstellung und Umwandlung von Athern," In: Houben-Weyl, Bd. VI/3, pp. 157-158 und 145-153.
T. Oh-e et al., "Palladium-Catalyzed Cross-Coupling Reaction of Organoboron Compounds with Organic Triflates," J. Org. Chem., 1993, 58, pp. 2201-2208.
N. Miyaura and Akira Suzuki: "Palladium-Catalyzed Cross-Coupling Reactions of Organoboron Compounds," Chem. Rev. 1995, 95, pp. 2457-2483.
Raymond McCague, Tetrahedron Letters, vol. 28, No. 6, pp. 701-702, 1987.
R.H. Summerville et al., Journal of the American Chemical Society, 1974, 96, pp. 1100-1110.
C.W. Schellhammer: Ketone aus Carbonsäuren und Aromaten in Gegenwart von Polyphosphoräure. In: Houben-Weyl, Bd. 7/2a, pp. 281, 299, 308 and 309, insbes.

(Continued)

*Primary Examiner*—Samuel Barts
(74) *Attorney, Agent, or Firm*—Millen, White, Zelano, Branigan, P.C.

(57) ABSTRACT

The invention relates to intermediate products and a new process for the production of benzocycloheptene C.

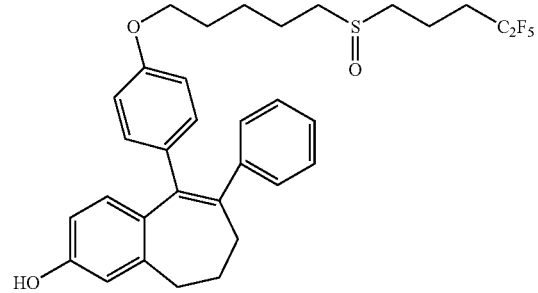

The process for the production of its new intermediate products according to the invention starts from economical starting materials, provides the intermediate stages in high yields and high purity, without chromatographic purification steps, and allows production on an industrial scale.

34 Claims, No Drawings

OTHER PUBLICATIONS

H.-J. Rimek: Katalytische Hydrierung am sp2-Kohlenstoff-Atom. In: Houben-Weyl, Bd. 4/1c, pp. 145-155 and 167-168.

H. Henecka: Säure—Basen-Katalyse. In: Houben-Weyl, Bd. IV/2 pp. 25-33.

Tetrahedron Asymmetry 1990, 1, 97-110.

P.J. Stang et al., "Behavior of Bent Vinyl Cations Generated by Solvolysis of Cyclic Trifluoromethanesulfonates," Journal of the American Chemical Society, 93:6, Mar. 24, 1971, pp. 1513-1516.

Database Crossfire Beilstein, Beilstein Institut Zur Förderung der Chemischen Wissenchaften, Frankfurt am Main, DE: Database accession No. Reaction ID 3136119, XP002230026.

Database Crossfire Beilstein, Beilstein Institut Zur Förderung der Chemischen Wissenchaften, Frankfurt am Main, DE: Database accession No. BRN 5565189, XP002230027.

Database Crossfire Beilstein, Beilstein Institut Zur Förderung der Chemischen Wissenchaften, Frankfurt am Main, DE: Database accession No. BRN 4010819, XP002230028.

* cited by examiner

SYNTHESIS OF OXYGEN-SUBSTITUTED BENZOCYCLOHEPTENES AS VALUABLE INTERMEDIATE PRODUCTS FOR THE PRODUCTION OF TISSUE-SELECTIVE ESTROGENS

This application claims the benefit of the filing date of U.S. Provisional Application Ser. No. 60/330,681 filed Oct. 29, 2001.

The invention relates to intermediate products and a new process for the production of benzocycloheptene C. The process for the production of its new intermediate products according to the invention starts from economical starting materials, provides the intermediate stages in high yields and high purity, without chromatographic purification steps, and allows large-scale production.

Compounds of general formula A (WO 00/03979) represent compounds with strong antiestrogenic action. In this case, these are selective estrogens, whose action occurs in a tissue-selective manner. The estrogenic action occurs in particular on bones. The advantage of this family of compounds is that no estrogenic action or only a slight estrogenic action occurs in the uterus and in the liver.

The compounds can also have antiestrogenic activity, which can be detected, for example, in an anti-uterus growth test or in tumor models.

Compounds with such a profile of action are designated as Selective Estrogen Receptor Modulators (SERMs). The most prominent representative of this family of compounds is raloxifene, which is now allowed as a medication for the prevention and the treatment of postmenopausal osteoporosis.

Since in general these are large-dose compounds, the provision of larger amounts of active ingredients is essential. The desire for a simple and economical synthesis in this family of substances is therefore especially pronounced.

The production of compounds of general formula A

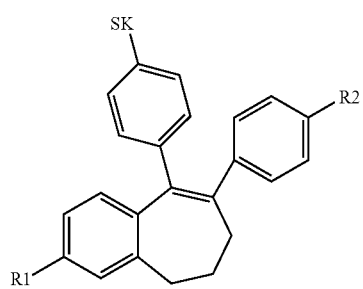

A is described in WO 00/03979.

In this case, SK, R1 and R2 stand for special side-chain radicals, which are specified in more detail in the above-mentioned application.

The object of this invention is to make available a more efficient process for the production of the compound of formula C (Example 9 in WO 00/03979).

The reaction to form target compound C is described as below in WO 00/03979 (See Examples 8 and 9):

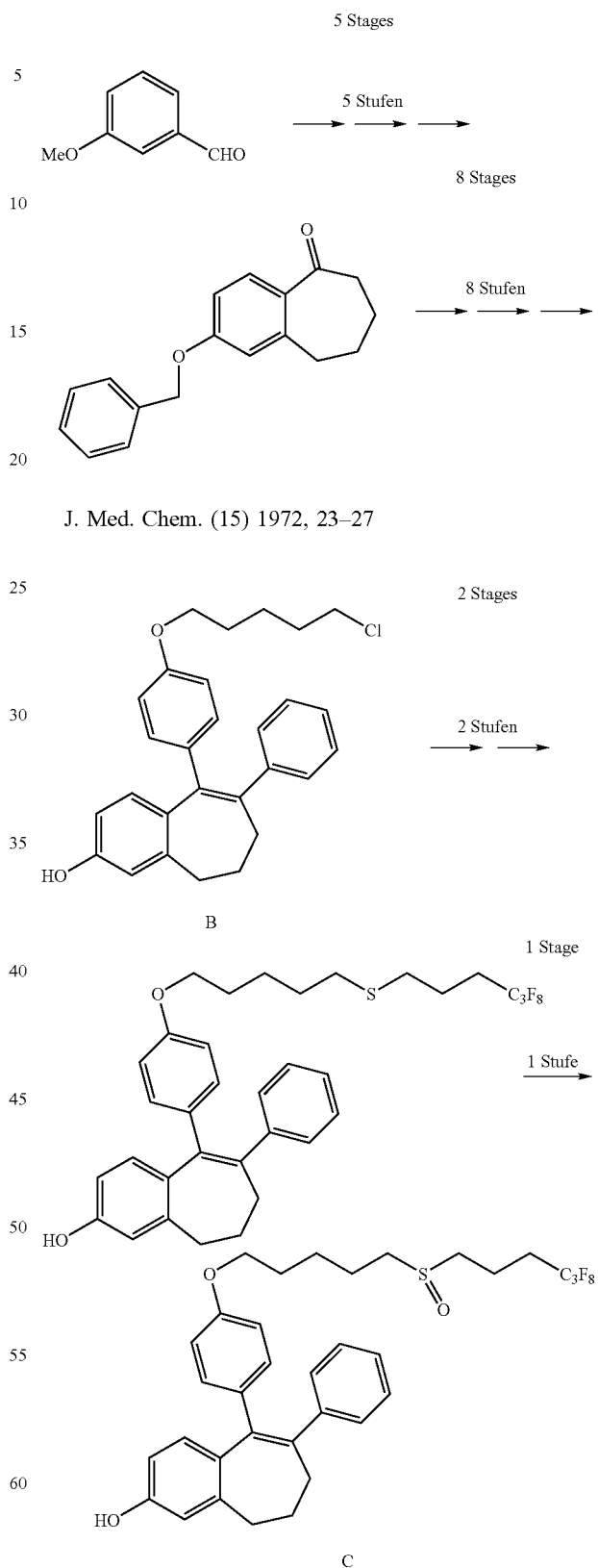

J. Med. Chem. (15) 1972, 23–27

B

C

The synthesis that is described in WO 00/03979 has a very high number of stages and contains several chromatographic purification steps. A scale-up of this synthesis with the goal of producing several 100 kg of compound C is associated with extreme difficulties.

The industrial-scale production therefore requires the development of a shorter and more effective synthesis sequence for the production of tissue-selective estrogens of general formula A of the compounds that are disclosed in WO 00/03979 and especially of Example 9 (here, C).

Relative to the synthesis laid open in WO 00/03979, the new process for the production of compound C according to the invention is distinguished in that a considerable shortening of the number of stages in central intermediate stage B is obtained. In this case, the sequence that is linked thereto in end product C remains unchanged.

Based on the simplified implementation (several one-pot processes), only 8 intermediate stages must be isolated in the production of C.

The table below shows a contrasting of the new process and the prior art.

|  | Σ-Stage Number | Chromatographies | Σ-Yield [%] |
| --- | --- | --- | --- |
| WO00/03979 | 16* | 2 | <6 |
| Process according to the invention*** | 8** | 0 | 36 |

*J. Med. Chem. (15) 1972, 23–27 was considered as well in this case
**Includes the production of phenyl-boronic acid
***See Example 1 of this application Another advantage of the process according to the invention lies in the fact that the products accumulate in high purities without chromatographic purification steps.

Moreover, the process according to the invention allows the introduction of additional aromatic compounds that are substituted with R2, by the intermediate stages of general formula I according to the invention being used

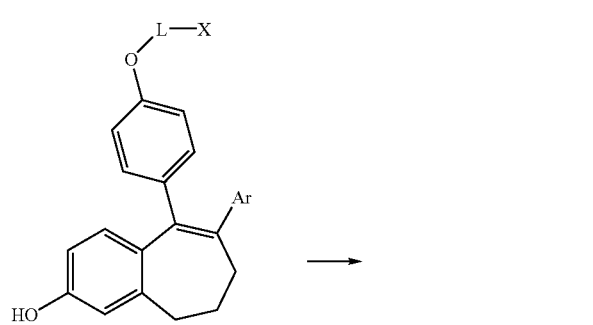

(I)

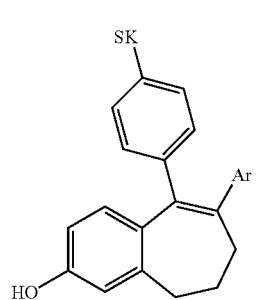

in which
L stands for a $C_2$–$C_{10}$ alkylene chain, which can be unbranched or branched,
X stands for Cl or Br,
Ar stands for an aromatic or heteroaromatic radical, which optionally can be substituted with up to 3 substituents.

The object of the invention is the preparation of compounds of general formula (I)

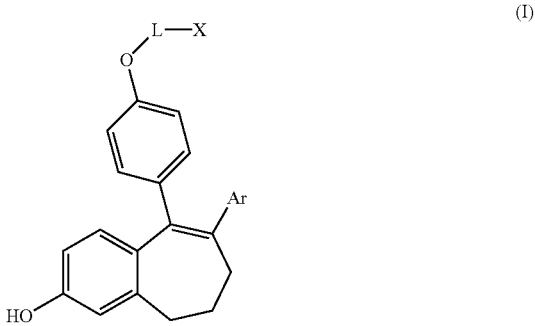

(I)

in which
L stands for a $C_2$–$C_{10}$ alkylene chain, which can be unbranched or branched,
X stands for Cl or Br,
Ar stands for an aromatic or heteroaromatic radical, which optionally can be substituted with up to 3 substituents.

After the production of these intermediate stages of general formula I, the reaction can be continued to form the end products of general formula A as described in WO 00/03979.

Compounds of general formula I are obtained from the methyl ethers of general formula II

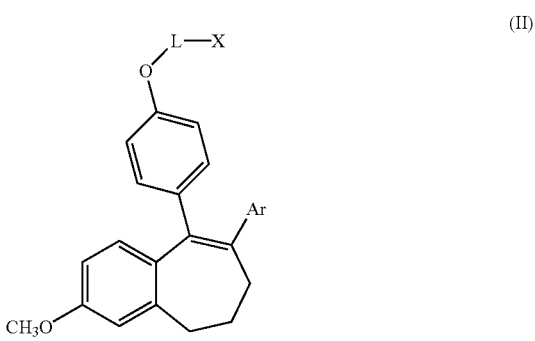

(II)

with L, X and Ar in the meaning that is indicated in general formula I, by selective cleavage of the methyl ether with a reagent that consists of boron tribromide and 2,6-dimethylpyridine (in a ratio of 1:1 to 1:1.5). The amount of reagent that is used can be between 1 and 6 equivalents (relative to bromine tribromide and to the aromatic methyl ether that is to be cleaved).

The reaction is performed in aprotic solvents, such as, e.g., dichloromethane, chloroform, 1,2-dichloromethane, but preferably in dichloromethane at temperatures of −30° C. to 50° C., preferably 10–30° C.

The very high selectivity of the aromatic methyl ether cleavage in the presence of higher aromatic alkyl ethers is surprising. In this case, the phenol products are obtained in high purity and in very good yield.

The use of BBr3 basically for cleavage of aromatic methyl ethers is known to one skilled in the art (Synthetic Communications, 9 (5), 407–410 (1979)). Without the addition of lutidine, the cleavage is carried out in an unselective manner (all aromatic ethers are cleaved). Only the combination with 2,6-lutidine yields the surprising selectivity.

Compounds of general formula II are produced from compounds of general formula III

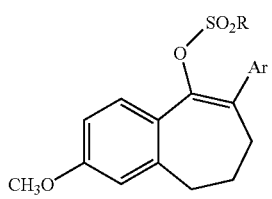

(III)

in which
Ar stands for an aromatic or heteroaromatic radical, which optionally can be substituted with up to 3 substituents,
R stands for a perfluorinated $C_1$–$C_8$ alkyl group, preferably $CF_3$, $C_4F_9$, $C_8F_{17}$, by reaction with phenylboronic acids of general formula IV

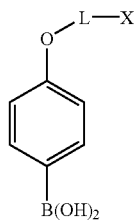

(IV)

in which
L and X have the meaning that is indicated in general formula I according to the methods of palladium-catalyzed Suzuki coupling that are known to one skilled in the art (J. Org. Chem. 1999, 64, 6797–6803/Chem. Rev. 1995, 95, 2457–2483/Pure Appl. Chem. 1991, 63, 419–422/Synlett 1990, 221–223/JOC 1993, 58, 2201–2208).

For this purpose, commercially available Pd catalysts, such as, e.g., Pd(PPh3)4 or Pd(Cl2) (PPh3)2, can be used (for additional catalysts, see, for example, Chemicals for Research, Metals, Inorganics and Organometallics in STREM-Katalog No. 18, 1999–2001).

Compounds of general formula III are obtained from ketones of general formula V

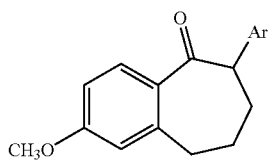

(V)

whereby
Ar has the meaning that is indicated in general formula I, by being reacted according to the methods for the production of enol triflates that are known to one skilled in the art (J. Amer. Chem. Soc.; EN; 96; 1974; 1100–1110/Chem. Ber.; GE; 110; 1977; 199–207/Tetrahedron Lett.; EN; 23; 1; 1982; 117–120/Synthesis; EN; 1; 1981; 29–30/Tetrahedron Lett.; EN; 40; 29; 1999; 5337–5340), with a reagent of general formula VI R—SO$_2$Nu  (VI)

in which
R has the meaning that is indicated in general formula III, and
Nu stands for a leaving group, such as, for example, F, Cl, I or R—SO$_3$.

The combination of nonafluorobutylsulfonyl fluoride with DBU in THF at 0° C. has proven especially advantageous. The nonaflates that are thus obtained are surprisingly stable and can, if desired, be isolated in solid form. In general, however, the crude product solutions are further reacted. Compounds of general formula VI are commercially available (Aldrich, Fluorochem, etc.).

Compounds of general formula IV can be produced from compounds of general formula VII

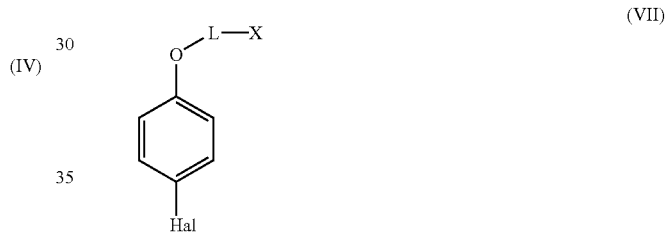

(VII)

whereby
L and X have the meaning that is indicated in general formula I, and
Hal stands for a halogen atom, such as Cl, Br, I according to the process for the production of phenylboronic acids from halo-aromatic compounds that is known to one skilled in the art (Houben Weyl, "Methoden der organischen Chemie [Methods of Organic Chemistry]," Volume 13/3a, pp. 637 ff. (1982), Georg Thieme Verlag Stuttgart, New York).

It has proven advantageous to use n-butyllithium for halogen metal exchange. Then, the lithium compound is reacted with B(OMe)3 and hydrolyzed with acid to form the desired phenylboronic acid derivative.

The production of the compounds of general formula VII is carried out according to the methods of phenol ether production that are familiar to one skilled in the art (Mol. Cryst. Liq. Cryst.; EN: 158; 1988; 209–240/Synth Commun.; EN; 28; 16; 1998; 3029–3040/J. Chem. Soc. Perkin Trans. 2; EN; 1989; 2041–2054) from the corresponding halophenols and the symmetric or unsymmetric dihaloalkanes (e.g., 5-bromo-1-chloropentane). The corresponding phenols and dihalides are commercially available.

The production of ketones of general formula V is described in Indian J. Chem., Vol 25B, August 1986, pp. 832–837 for the case in which Ar stands for the phenyl radical. The sequence for the production of this intermediate stage that is described there is very long and can be implemented with great difficulty on the industrial scale.

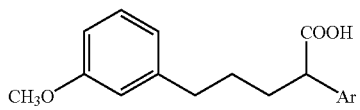
(VIII)

Especially in technical implementation and scale-up, however, it has proven very advantageous when compounds of general formula V are implemented from compounds of general formula VIII
with Ar in the meaning that is mentioned in general formula I according to the ring-closure process of Friedel-Crafts that is known to one skilled in the art (Chem. Rev. 70, 553 (1970)).

The use of polyphosphoric acid in the temperature range of 80–120° C. can be mentioned as especially preferred. The polyphosphoric acid can be purchased or else freshly prepared.

The production of the compounds of general formula VIII is carried out in a way that is known in the art from compounds of general formula IX

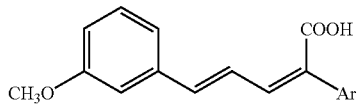
(IX)

by catalytic hydrogenation (Houben Weyl, "Methoden der organischen Chemie," Volume 4/1c Part 1, pp. 14 ff (1980), Georg Thieme Verlag Stuttgart, New York).

Compounds of general formula VIII can be obtained in a single-pot reaction starting from 3-methoxybenzaldehyde,

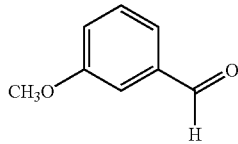

which is reacted by base-catalyzed reaction with acetaldehyde to form 3-methoxy-cinnamaldehyde (organic Reactions, Vol. 16 (1968), pp. 1 ff/Justus Liebigs Ann. Chem.; 412; 1917; 322)

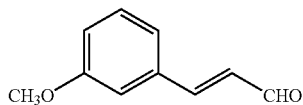

and is reacted without isolation in a subsequent Knoevenagel reaction with a compound of general formula X

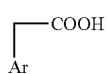
(X)

with Ar in the meaning that is indicated in general formula I (Organic Reactions, Vol. 15 (1967), pp. 204 ff.).

Compounds of general formula X are commercially available (e.g, Aldrich, Fluka, etc.) or can be easily obtained according to the process for the production of arylacetic acids that is known to one skilled in the art (J. Amer. Chem. Soc.; 78; 1956; 6037/Can. J. Chem.; EN; 70; 3; 1992; 992–999/J. Amer. Chem. Soc.; EN; 112; 5; 1990; 1894–1896/Recl. Trav. Chim. Pays-Bas; 70; 1951; 977, 983/J. Amer. Chem. Soc.; 69; 1947; 1797).

It has proven advantageous in the production of cinnamaldehyde to use an inorganic base, such as NaOH, KOH, preferably KOH. The reaction occurs in water at temperatures of between 1–30° C. Up to 5 equivalents of acetaldehyde can be used. It has proven especially advantageous to add the acetaldehyde and the base in small portions and to wait in the meantime 10 to 30 minutes before each further addition.

For the Knoevenagel reaction, preferably acetic anhydride and triethylamine are used as a base. The reaction temperature is between 60° C. and reflux.

The process according to the invention is also suitable for the production of compounds of general formula XI

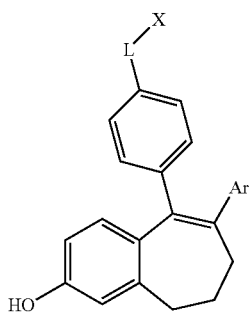
(XI)

in which

Ar, L and X have the meanings that are indicated in general formula I, by beginning and proceeding analogously from the corresponding haloalkane-haloaromatic compounds of general formula XII

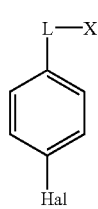
(XII)

instead of the halophenols of general formula VII.

The compounds of general formula XII are known in the literature and are partially commercially available.

As preferred radicals L, there can be mentioned by way of example:

—$C_2H_4$—, —$C_3H_6$—, —$CH_2$—$CH(CH_3)$—$CH_2$—, —$C_4H_8$—, —$C_5H_{10}$—, —$C_6H_{12}$—, —$C_7H_{14}$—, —$C_8H_{16}$—.

Especially preferred is the —$C_5H_{10}$ radical.

A chlorine atom preferably stands for X.

Some examples can be mentioned below for radical Ar:

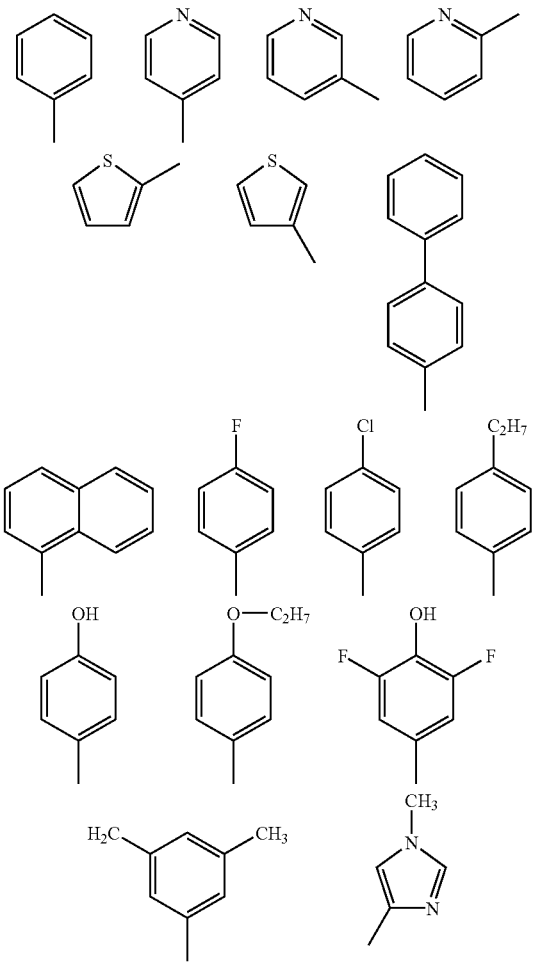

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

Especially preferred here are the phenyl radical, the pyridyl radical and the thiophene radical.

The invention is explained by the subsequent examples.

EXAMPLE 1

Example 1a (2Z,4E)-5-(3-Methoxyphenyl)2-phenylpentadiene-2,4-dienoic acid 310 ml of 20% aqueous potassium hydroxide solution is added to 750 g (5.5 mol) of 3-methoxybenzaldehyde in 3750 ml of water. 160 ml of acetaldehyde, dissolved in 450 ml of water over 30 minutes, is then added in drops such that the internal temperature does not exceed 30° C. Then, this process is repeated 7 times (first 310 ml of 20% aqueous KOH, then 160 ml of acetaldehyde/450 ml of water/30 minutes).

After the last addition is completed, it is stirred for 30 minutes at room temperature. 3750 ml of methyl-tert-butyl ether is added, and it is thoroughly stirred for 15 minutes. The organic phase is separated and mixed with 250 ml of glacial acetic acid/250 ml of water. It is stirred for 5 minutes. Then, 1500 ml of water is added, and it is stirred for another 5 minutes. The organic phase is separated and then evaporated to the dry state in a vacuum.

748.80 g (5.5 mol) of phenylacetic acid, 1000 ml of acetic acid anhydride and 1470 ml of triethylamine are added to the residue (orange-colored oil) and heated for 4 hours to 100° C.

The solvent is distilled off at 15 mbar, then it is allowed to come to room temperature. The residue is dissolved in 2500 ml of methyl-tert-butyl ether. It is cooled to 0° C., and 600 ml of concentrated hydrochloric acid is slowly added in drops. Then, 200 ml of water is added to it, and it is stirred for 5 minutes. The organic phase is separated and mixed with 1100 ml of 50% aqueous sodium hydroxide solution. Then, 830 ml of water is added. It is thoroughly and vigorously stirred for 30 minutes, and the water phase is separated (product in water phase). The organic phase is absorptively precipitated again with 1100 ml of sodium hydroxide solution and 830 ml of water. The water phase is separated and combined with the first water phase.

1700 ml of methyl-tert-butyl ether is added to the thus combined water phases and thoroughly and vigorously stirred for 5 minutes. The aqueous phase is separated and set at pH 1.5 with concentrated hydrochloric acid. The precipitated acid is extracted with 4000 ml of methyl-tert-butyl ether. The organic phase is evaporated to the dry state in a vacuum. Then, 2000 ml of ethanol is added, and about 1000 ml of ethanol is distilled off in a vacuum. 1000 ml of ethanol is added again, and the deposited precipitate is absorptively precipitated for one hour at 0° C.

Precipitate is filtered out and rewashed with 350 ml of cold ethanol. The light yellow solid is dried in a vacuum at 40° C.

Yield: 1094 g (71% of theory) of a light yellow solid.

Elementary analysis:

| Cld. | C 77.12 | H 5.75 |
|---|---|---|
| Fnd. | C 77.23 | H 5.84 |

Example 1b 5-(3-Methoxyphenyl)-2-phenyl-pentanoic acid 1000 g (3.567 mol) of the title compound of Example 1a is dissolved in 8 l of tetrahydrofuran, and 75 g of palladium catalyst (10% Pd/C) is added. It is hydrogenated at room temperature (2 bar).

Catalyst is filtered out, it is rewashed with 500 ml of tetrahydrofuran, and the solution is evaporated to the dry state in a vacuum.

Yield: 1015 g (100% of theory) of a colorless, viscous oil.
Elementary analysis:

| Cld. | C 76.03 | H 7.09 |
|------|---------|--------|
| Fnd. | C 76.12 | H 7.15 |

Example 1c

7-Methoxy-2-phenyl-1-benzosuberone 5.6 kg of 115% polyphosphoric acid is added to 560 g (1.97 mol) of the title compound of Example 1b, and it is heated for 3 hours to 95° C.

It is allowed to cool to 50° C., and the solution that is still warm is poured into 9 l of ice water. Then, 5000 ml of methyl-tert-butyl ether is added and stirred intensively for 10 minutes. The organic phase is separated, and the water phase is rewashed again with 1500 ml of methyl-tert-butyl ether.

The combined organic phases are washed once with 4000 ml of water, then with 1200 ml of 5% aqueous sodium hydroxide solution. The organic phase is separated and mixed with 280 g of activated carbon. It is refluxed for 2 hours. The activated carbon is filtered off, rewashed with a little methyl-tert-butyl ether, and the filtrate is evaporated to the dry state in a vacuum.

Yield: 456.5 g (87% of theory) of a colorless oil, which crystallizes when allowed to stand.
Elementary analysis:

| Cld. | C 81.17 | H 6.81 |
|------|---------|--------|
| Fnd. | C 81.29 | H 7.02 |

Example 1d

4-[(5-Chloropentyl)oxy]phenylboronic acid 1000 g (5.78 mol) of 4-bromophenol, 1125.7 g (6.069 mol) of 1-bromo-5-chloropentane and 1118.3 g (8.092 mol) of potassium carbonate are added to 4000 ml of dimethylformamide and stirred for 5 hours at 60° C.

It is cooled to 20° C., and 3500 ml of toluene is added. Precipitated salts are filtered out. The salts are rewashed 3 times with 3500 ml of toluene each.

The DMF/toluene filtrate is mixed with 4000 ml of water and absorptively precipitated for 5 minutes. The toluene phase is separated, and the aqueous phase is rewashed once with 3000 ml of toluene.

The toluene phases are combined and then absorptively precipitated with 4000 ml of 5% aqueous sodium hydroxide solution. The toluene phase is separated, washed with 4000 ml of water and then evaporated to the dry state in a vacuum.

The residue is dissolved in 9 l of tetrahydrofuran and cooled to −65° C. (internal temperature). Then, 2860 ml of n-butyllithium solution (1.6 mol in hexane) is slowly added in drops so that the temperature does not exceed −60° C. It is stirred for 30 more minutes at −65° C.

Then, 1291 g of boric acid trimethyl ester is added in drops to it and stirred for 2 more hours at −65° C. Then, it is heated to −20° C.

For working-up, a solution that consists of 2200 ml of water/methanol 1:1 is carefully added in drops, so that the temperature does not exceed −15° C. After the addition is completed, 11 liters of 2N aqueous hydrochloric acid is carefully added and then stirred for one hour at 0° C. It is allowed to come to room temperature, the organic phase is separated, and the water phase is extracted once with 5000 ml and then with 2000 ml of methanol-tert-butyl ether.

The organic phases are combined and absorptively precipitated with 11 liters of 2N sodium hydroxide solution (30 minutes). The water phase is separated (product) and washed twice with 3000 ml of methyl-tert-butyl ether. The water phase is set at pH 1 by adding 6N hydrochloric acid, then 6000 ml of methyl-tert-butyl ether is added, and it is stirred for 2 hours at room temperature.

The organic phase is separated, washed once with 3000 ml of water and then evaporated to the dry state in a vacuum.

Yield: 1219.5 g (87% of theory) of a rose-colored solid.
Elementary analysis:

| Cld. | C 68.45 | H 6.73 | Cl 6.97 | B 2.12 |
|------|---------|--------|---------|--------|
| Fnd. | C 68.59 | H 6.84 | Cl 6.89 | B 2.03 |

Example 1e

5-{4-[(5-Chloropentyl)oxy]phenyl}-2-methoxy-6-phenyl-8,9-dihydro-7H-benzocycloheptene 81.67 g (306.64 mmol) of the title compound of Example 1c is dissolved in 400 ml of tetrahydrofuran/methyl-tert-butyl ether, and the solution is cooled to 3° C. 56.02 g of diazabicycloundecane DBU (367.97 mmol) is added to it, whereby the temperature is kept at 3°. It is rinsed with 40 ml of THF. Then, 111.46 g of perfluorobutane-1-sulfonic acid fluoride (367.97 mmol) is added to it (at 3° C.), rinsed with 40.86 ml of methyl-tert-butyl ether, whereby the temperature should not exceed 8° C. during the addition. Then, it is stirred for 12 hours at 3° C. 290 ml of 10% potassium carbonate solution (3.5-fold on educt) is added to the reaction solution at 10° C., and it is stirred for 5 minutes. The organic phase is separated and concentrated by evaporation in a vacuum to a volume of about 500 ml. The crude nonaflate solution that is thus obtained is then used in the next step.

78.08 g of the title compound of Example 1d (321.97 mmol) is dissolved in 390 ml of MTB at room temperature, and 310 ml of 2 M aqueous K2CO3 solution is added. Then, 1.076 g of bis-(triphenylphosphine)-palladium(II) chloride (1.533 mmol, 0.005 MEq) in 10 ml of methyl-tert-butyl ether is suspended. Then, the above-produced nonaflate solution is added to it, and it is refluxed for 30 minutes. It is cooled to room temperature and mixed with 455 ml of 2N aqueous NaOH. Then, it is stirred for 15 minutes at room temperature. The organic phase is stirred with 455 ml of 2N aqueous HCl for 15 minutes at room temperature. The organic phase is separated and mixed with 15 g of activated carbon. It is refluxed briefly, and the still warm solution is filtered off on diatomaceous earth. Then, it is rinsed twice with 100 ml each of methyl-tert-butyl ether. The filtrate is concentrated by evaporation in a vacuum at 40° C. 455 ml of methanol is added to the residue, and the precipitate that is produced is absorptively precipitated for 6 hours at room temperature. The suspension is cooled to 5° C., filtered off and rinsed with 100 ml of cold methanol. It is dried at 40° C. in a vacuum.

Yield: 112.4 g (82% of theory) of a colorless, crystalline solid.

Elementary analysis:

| Cld. | C 77.92 | H 6.99 | Cl 7.93 |
|------|---------|--------|---------|
| Fnd. | C 78.07 | H 7.10 | Cl 7.87 |

Example 1f

5-{4-[(5-Chloropentyl)oxy]phenyl}-6-phenyl-8,9-dihydro-7H-benzocyclohepten-2-ol 127.51 g of boron tribromide (508.93 mmol) is dissolved at room temperature in 650 ml of dichloromethane. A solution that consists of 57.26 g of 2,6-dimethylpyridine (534.37 mmol) in 320 ml of dichloromethane is slowly added to it at 0° C. (it is advisable that the temperature remain at 0° C.). It is cooled to 0° C. It is allowed to heat to 20° C., and then a solution that consists of 65.00 g (145.4 mmol) of the title compound of Example 1e (dissolved in 300 ml of dichloromethane) is added in drops, and in this case, the internal temperature should not exceed 20° C. It is stirred for 4 more hours at 20° C. The solution is cooled to 0° C., and a mixture that consists of 10 ml of water and 65 ml of tetrahydrofuran is carefully added in drops while being stirred vigorously.

Then, another 1250 ml of water is carefully added to the reaction solution, and it is stirred for 30 more minutes at 20° C. The organic phase is separated, and the water phase is subsequently re-extracted with 325 ml of dichloromethane. The organic phase is separated. Both organic phases are combined and mixed with 13 g of $NaHCO_3$ and 312 ml of water. The organic phase is stirred with the $NaHCO_3$ solution for 30 minutes at 20° C. The organic phase is separated and concentrated by evaporation in a vacuum to about 300 ml (crystallization begins even before the desired volume is reached). The crystal suspension is mixed with 300 ml of acetone, and about 320 ml of solvent is distilled off at 40° C./300 mbar. Then, it is stirred for one hour at 0° C. The crystals are filtered off and washed with a little cold acetone. After concentration by evaporation, another crystal fraction is obtained from the mother liquor.

Yield: 51.6 g (82% of theory) of a colorless, crystalline powder

Elementary analysis:

| Cld. | C 77.67 | H 6.75 | Cl 8.19 |
|------|---------|--------|---------|
| Fnd. | C 77.54 | H 6.92 | Cl 8.03 |

Example 1g 5-(4-{5-[(4,4,5,5,5-Pentafluoropentyl)sulfanyl]pentyloxy}-phenyl)-6-phenyl-8,9-dihydro-7H-benzocyclohepten-2-ol 100 g (230.9 mmol) of the title compound of Example if and 132.1 g (881.1 mmol) of sodium iodide are refluxed in 1000 ml of methyl ethyl ketone (MEK) for 16 hours. Then, about 650 ml of solvent is distilled off under reduced pressure, and it is mixed with 1500 ml of water. It is allowed to stir for 15 minutes at room temperature, the deposited precipitate is filtered off, and it is washed with a mixture that consists of cold 240 ml of ethanol/160 ml of water. The still somewhat wet precipitate is dissolved in 1200 ml of tetrahydrofuran. At normal pressure, 400 ml of tetrahydrofuran is distilled off, and 400 ml of methanol is added.

Another solution is added to this solution that was prepared in a separate flask as follows: 64.8 g (274.2 mmol) of 4,4,5,5,5-pentafluoropentylthioacetate is dissolved under a nitrogen atmosphere in 300 ml of methanol, and 51 ml of 30% sodium methanolate solution (in MeOH) is added to it at room temperature. It is stirred for 30 minutes at room temperature.

After the two solutions have been combined, it is allowed to stir for one more hour at room temperature.

For working-up, it is concentrated by evaporation in a vacuum up to a residual volume of about 350 ml. 800 ml of water is added to the residue and stirred for 30 minutes at 10° C. It is filtered off and rewashed with a mixture that consists of 360 ml of water/40 ml of methanol. Then, it is dried in a vacuum at 40° C.

Yield: 124.1 g (91% of theory) of a colorless, finely crystalline powder.

Elementary analysis:

| Cld. | C 67.10 | H 5.97 | S 5.43 | F 16.08 |
|------|---------|--------|--------|---------|
| Fnd. | C 66.95 | H 6.11 | S 5.33 | F 15.92 |

Example 1h 5-(4-{5-[(RS)-(4,4,5,5,5-Pentafluoropentyl)sulfinyl]pentyloxy}-phenyl)-6-phenyl-8,9-dihydro-7H-benzocyclohepten-2-ol 100 g (169.3 mmol) of the title compound of Example 1g is dissolved in 800 ml of acetone/500 ml of methanol. Then, 175 ml of water is carefully added. Then, 36.20 g (169.3 mmol) of sodium periodate is added, and it is stirred for 16 hours at room temperature.

1000 ml of dichloromethane and 1300 ml of water are added and stirred thoroughly for 30 minutes at room temperature. The organic phase is separated and concentrated by evaporation to one-half of its original volume in a vacuum. 950 ml of toluene is added to the residue, and the lower-boiling components are carefully distilled off at normal pressure (dichloromethane, methanol). Then, it is heated up until about 50 ml of toluene distills over. It is allowed to come to room temperature, whereby the product crystallizes out. It is stirred for 30 minutes at 10° C., and the deposited precipitate is filtered off. It is rewashed twice with a little cold toluene and then dried in a vacuum at 50° C.

Yield: 99.6 g (97% of theory) of a colorless, crystalline powder.

Elementary analysis:

| Cld. | C 65.33 | H 5.81 | S 5.28 | F 15.66 |
|------|---------|--------|--------|---------|
| Fnd. | C 65.56 | H 5.93 | S 5.12 | F 15.47 |

Other Examples that Demonstrate the Production of the Universal Intermediate Compound of General Formula I In the tables below, the yields and elementary analyses of other examples are indicated. These can be produced analogously to what was described under Example 1.

Analogously to Example 1a, another arylacetic acid was used instead of phenylacetic acid:

| Arylacetic acid Ar—CH2—COOH | MeO-C6H4-CH=CH-CH=C(COOH)-Ar | Yield: % of theory |
|---|---|---|
| 4-pyridyl-CH2-COOH | Cld. C 72.58 H 5.37 N 4.98<br>Fnd. C 72.43 H 5.41 N 4.87 | 61 |
| 3-pyridyl-CH2-COOH | Cld. C 72.58 H 5.37 N 4.98<br>Fnd. C 72.40 H 5.48 N 4.83 | 59 |
| 2-pyridyl-CH2-COOH | Cld. C 72.58 H 5.37 N 4.98<br>Fnd. C 72.38 H 5.51 N 4.80 | 57 |
| 4-F-C6H4-CH2-COOH | Cld. C 72.47 H 5.07 F 6.37<br>Fnd. C 72.34 H 5.16 F 6.25 | 70 |
| 2-thienyl-CH2-COOH | Cld. C 67.11 H 4.93 S 11.20<br>Fnd. C 67.01 H 5.12 S 11.04 | 63 |

Analogously to Example 1b, the hydrogenation of the double-bond system was performed:

| Ar | MeO-C6H4-(CH2)3-CH(COOH)-Ar | Yield: % of theory |
|---|---|---|
| 4-pyridyl | Cld. C 71.56 H 6.71 N 4.91<br>Fnd. C 71.48 H 6.81 N 4.87 | 99 |
| 3-pyridyl | Cld. C 71.56 H 6.71 N 4.91<br>Fnd. C 71.43 H 6.85 N 4.83 | 100 |
| 2-pyridyl | Cld. C 71.56 H 6.71 N 4.91<br>Fnd. C 71.40 H 6.88 N 4.80 | 100 |
| 4-F-C6H4 | Cld. C 71.51 H 6.33 F 6.28<br>Fnd. C 71.62 H 6.44 F 6.21 | 100 |
| 2-thienyl | Cld. C 66.18 H 6.25 S 11.04<br>Fnd. C 66.03 H 6.43 S 10.92 | 99 |

Analogously to Example 1c, the ring closure in the benzosuberones was performed:

Table 1: Ar–[benzosuberone with MeO]

| Ar | Analysis | Yield: % of theory |
|---|---|---|
| 4-pyridyl | Cld. C 76.38 H 6.41 N 5.24<br>Fnd. C 76.29 H 6.55 N 5.13 | 85 |
| 3-pyridyl | Cld. C 76.38 H 6.41 N 5.24<br>Fnd. C 76.23 H 6.64 N 5.10 | 86 |
| 2-pyridyl | Cld. C 76.38 H 6.41 N 5.24<br>Fnd. C 76.26 H 6.50 N 5.17 | 81 |
| 4-F-phenyl | Cld. C 76.04 H 6.03 F 6.68<br>Fnd. C 75.91 H 6.12 F 6.63 | 87 |
| 2-thienyl | Cld. C 70.56 H 5.92 S 11.77<br>Fnd. C 70.45 H 6.05 S 11.68 | 82 |

Analogously to Example 1e, the Suzuki couplings were performed via the nonaflates:

| Ar | Analysis | Yield: % of theory |
|---|---|---|
| 4-pyridyl | Cld. C 75.07 H 6.75 N 3.13 Cl 7.91<br>Fnd. C 74.87 H 6.85 N 3.02 Cl 7.83 | 76 |
| 3-pyridyl | Cld. C 75.07 H 6.75 N 3.13 Cl 7.91<br>Fnd. C 74.83 H 6.83 N 3.11 Cl 7.80 | 80 |
| 2-pyridyl | Cld. C 75.07 H 6.75 N 3.13 Cl 7.91<br>Fnd. C 74.85 H 6.80 N 3.04 Cl 7.85 | 76 |
| 4-F-phenyl | Cld. C 74.91 H 6.50 F 4.09 Cl 7.62<br>Fnd. C 74.87 H 6.61 F 4.01 Cl 7.55 | 81 |
| 2-thienyl | Cld. C 71.58 H 6.45 S 7.08 Cl 7.83<br>Fnd. C 71.49 H 6.55 S 6.98 Cl 7.75 | 75 |

Analogously to Example 1f, the methyl ether cleavages were performed with BBr3/2,6-lutidine:

| Ar | Analysis | Yield: % of theory |
|---|---|---|
| 4-pyridyl | Cld. C 74.73 H 6.50 N 3.23 Cl 8.17<br>Fnd. C 74.66 H 6.63 N 3.15 Cl 8.08 | 77 |
| 3-pyridyl | Cld. C 74.73 H 6.50 N 3.23 Cl 8.17<br>Fnd. C 74.61 H 6.61 N 3.10 Cl 8.11 | 78 |
| 2-pyridyl | Cld. C 74.73 H 6.50 N 3.23 Cl 8.17<br>Fnd. C 74.58 H 6.70 N 3.07 Cl 8.05 | 74 |
| 4-F-phenyl | Cld. C 77.58 H 6.73 F 4.23 Cl 7.90<br>Fnd. C 77.45 H 6.87 F 4.13 Cl 7.81 | 88 |
| 2-thienyl | Cld. C 74.20 H 6.69 S 7.34 Cl 8.11<br>Fnd. C 74.09 H 6.79 S 7.25 Cl 8.02 | 75 |

The entire disclosure s of all applications, patents and publications, cited herein and of corresponding German application No. 101 51 095.0, filed Oct. 12, 2001 and U.S. Provisional Application Ser. No. 60/330,681, filed Oct. 29, 2001, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for the production of compounds of formula I

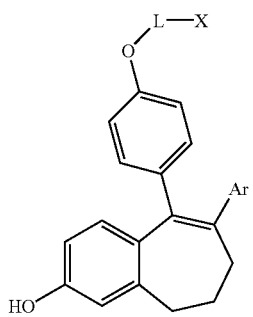

in which
L is a $C_2$–$C_{10}$ alkylene chain, which can be unbranched or branched,
X is Cl or Br,
Ar is an aromatic or heteroaromatic radical, which optionally can be substituted with up to 3 substituents,
said process comprising:
cleaving the aromatic methyl ether in a compound of formula II

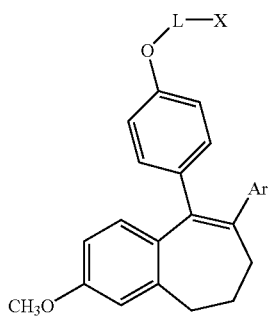

with a reagent comprising boron tribromide and 2,6-dimethylpyridine.

2. A process for the production of compounds of formula II

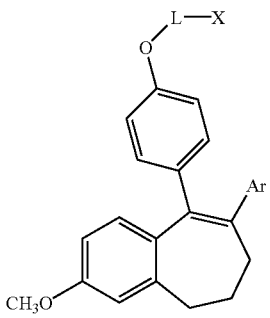

in which
L is a $C_2$–$C_{10}$ alkylene chain, which can be unbranched or branched,
X is Cl or Br,
Ar is an aromatic or heteroaromatic radical, which optionally can be substituted with up to 3 substituents,
said process comprising:
reacting a compound of formula III

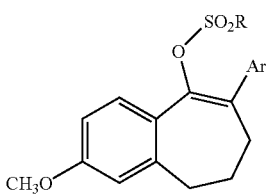

in which
Ar is an aromatic or heteroaromatic radical, which optionally can be substituted with up to 3 substituents,
R is a perfluorinated, straight-chain $C_1$–$C_8$ alkyl group,
with a compound of formula IV

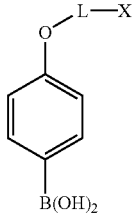

in which
L is a $C_2$–$C_{10}$ alkylene chain, which can be unbranched or branched,
X is Cl or Br,
under palladium catalysis.

3. A process for the production of compounds of formula III

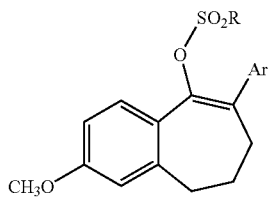
(III)

in which
- Ar is an aromatic or heteroaromatic radical, which optionally can be substituted with up to 3 substituents,
- R is a perfluorinated, straight-chain $C_1$–$C_8$ alkyl group, said process comprising:
reacting a compound of formula V

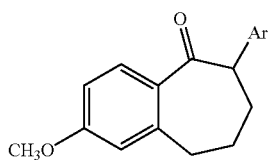
(V)

with a compound of formula VI

(VI)

in which
- R is a perfluorinated, straight-chain $C_1$–$C_8$ alkyl group,
- Nu is a leaving group, in the presence of an organic or inorganic base in an aprotic solvent.

4. A process for the production of compounds of formula IX

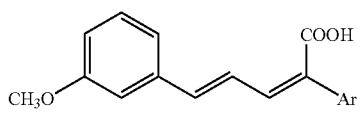
(IX)

in which
- Ar is an aromatic or heteroaromatic radical, which optionally can be substituted with up to 3 substituents, said process comprising:
reacting 3-methoxybenzaldehyde and acetaldehyde under base catalysis to produce 3-methoxycinnamaldehyde which is then reacted in a subsequent Knoevenagel condensation with an arylacetic acid of formula X

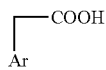
(X)

5. A process according to claim 1, wherein Ar is one of the following radicals:

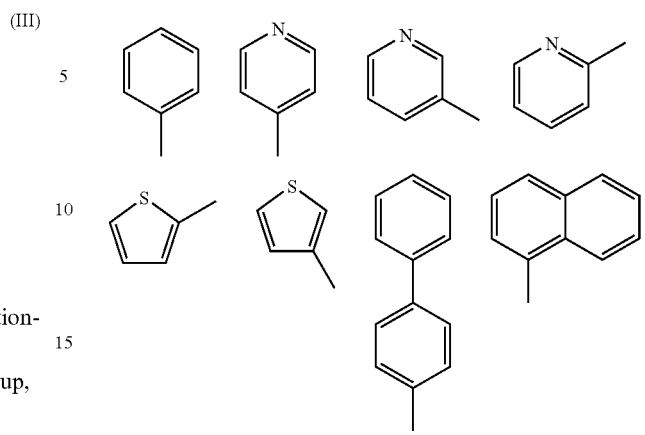

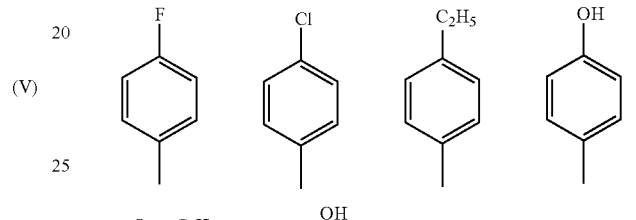

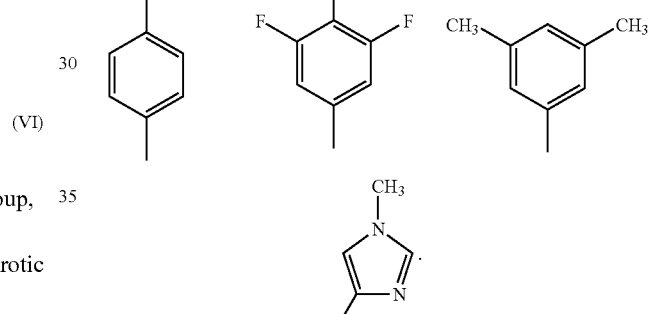

6. A process according to claim 5, wherein Ar a phenyl radical, pyridyl radical or thiophene radical.

7. A compound of formula III

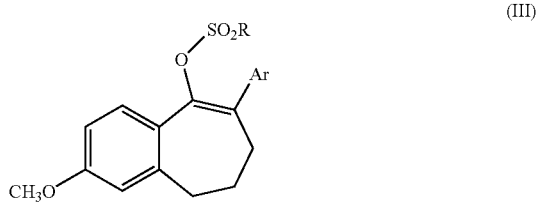
(III)

in which
- Ar is an aromatic or heteroaromatic radical, which optionally can be substituted with up to 3 substituents, and
- R is a perfluorinated $C_1$–$C_8$ alkyl group.

8. A process comprising:
reacting 3-methoxybenzaldehyde and acetaldehyde under base catalysis to produce 3-methoxycinnamaldehyde which is then reacted in a subsequent Knoevenagel condensation with an arylacetic acids of formula X

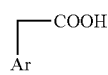

whereby a compound of formula IX is produced,

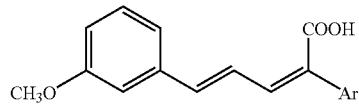

in which
- Ar is an aromatic or heteroaromatic radical, which optionally can be substituted with up to 3 substituents;

hydrogenating said compound of formula IX to obtain a compound of formula VIII

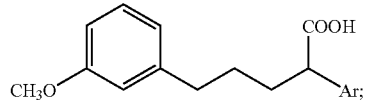

cyclizing the compound of formula VIII with polyphosphoric acid to obtain a compound of formula V

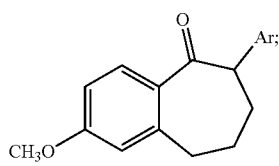

reacting under palladium catalysis the compound of formula V with a compound of formula VI R—SO$_2$Nu    (VI)

in which
- R is a perfluorinated, straight-chain C$_1$–C$_8$-alkyl group,
- Nu is a leaving group, in the presence of an organic or inorganic base in an aprotic solvent to obtain a compound of formula III

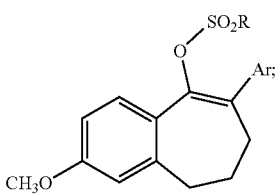

reacting the compound of formula III with a compound of formula IV

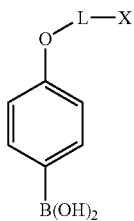

in which
- L is a C$_2$–C$_{10}$ alkylene chain, which can be unbranched or branched,
- X is Cl or Br, to obtain a compound of formula II

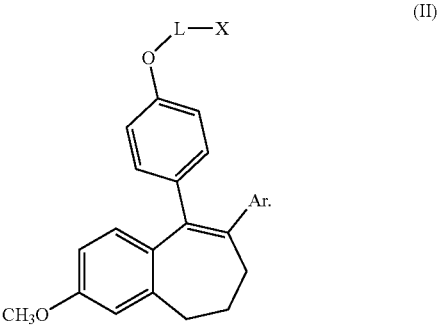

9. A process according to claim 8, wherein, in formula II, L-X is 5-chloropentyl and Ar is phenyl, said process further comprising:
- cleaving the methyl ether of formula II using boron tribromide in 2,6-dimethylpyridine,
- treating the resultant compound with sodium iodide in methyl ethyl ketone,
- reacting the resultant compound with 4,4,5,5,5-pentafluoropentylthioacetate, and then treating the resultant compound with sodium periodate in the presence of dichloromethane to obtain the following compound

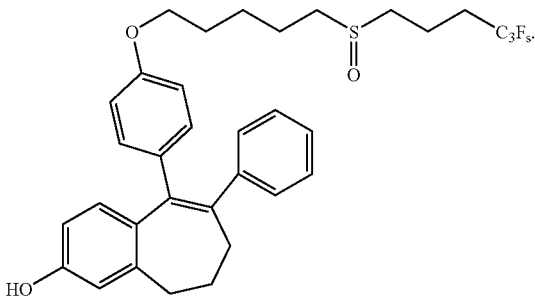

10. A process according to claim 2, wherein the palladium-catalyst complex that is used contains either Pd(O) or Pd(II) in the complex.

11. The compound of the formula:

[chemical structure with SO₂C₄F₉, phenyl, and CH₃O groups on a benzocycloheptene]

12. The compound of the formula:

[chemical structure showing CH₃O-phenyl-CH=CH-C(COOH)=CH-phenyl diene]

13. A process for gentle and selective cleavage of aromatic methyl ethers comprising: reacting an aromatic methyl ether with a reagent comprising boron tribromide and 2,6-dimethylpyridine.

14. A process for gentle and selective cleavage of a methyl ether on an aromatic compound which further contains an ether group containing a $C_2$–$C_{10}$ alkylene chain comprising: reacting the aromatic compound with a reagent-comprising boron tribromide and 2,6-dimethylpyridine.

15. A reagent consisting of boron tribromide and 2,6-dimethylpyridine.

16. A process according to claim 2, wherein R is $CF_3$, $C_4F_9$, or $C_8F_{17}$.

17. A process according to claim 3, wherein R is $CF_3$, $C_4F_9$, or $C_8F_{17}$.

18. A process according to claim 7, wherein R is $CF_3$, $C_4F_9$, or $C_8F_{17}$.

19. A process according to claim 3, wherein Nu is F, Cl, I or R—$SO_3$.

20. A process according to claim 9, wherein L is a $C_5$ alkylene chain.

21. A process according to claim 1, wherein said reagent contains boron tribromide and 2,6-dimethylpyridine in a ratio of 1:1 to 1:1.5.

22. A process according to claim 1, wherein the amount of said reagent used is between 1 and 6 equivalents, relative to bromine tribromide and the aromatic methyl ether that is to be cleaved.

23. A process according to claim 1, wherein the reaction is performed in an aprotic solvent at a temperature of −30° C. to 50° C.

24. A process according to claim 4, wherein NaOH or KOH is used as the base for the base catalysis.

25. A process according to claim 4, wherein the reaction takes place in water at a temperature of between 1–30° C.

26. A process according to claim 4, wherein in the Knoevenagel condensation acetic anhydride and triethylamine are used as a base.

27. A process according to claim 1, wherein L is —$C_2H_4$—, —$C_3H_6$—, $CH_2$—$CH(CH_3)$—$CH_2$, —$C_4H_8$—, —$C_5H_{10}$—, —$C_6H_{12}$—, —$C_7H_{14}$—, or —$C_8H_{16}$—.

28. A process according to claim 2, wherein L is —$C_2H_4$—, —$C_3H_6$—, $CH_2$—$CH(CH_3)$—$CH_2$, —$C_4H_8$—, —$C_5H_{10}$—, —$C_6H_{12}$—, —$C_7H_{14}$—, or —$C_8H_{16}$—.

29. A process for the production of compounds of formula V

[chemical structure (V): benzocycloheptanone with CH₃O and Ar substituents]

wherein Ar is selected from the following radicals:

[six heteroaryl radicals: 4-methylpyridin-yl, 3-methylpyridin-2-yl (or similar), 2-methylpyridinyl, 2-methylthienyl, 3-methylthienyl, and N-methylimidazolyl]

said process comprising:
reacting a compound of formula VIII with polyphosphoric acid

[chemical structure (VIII): CH₃O-phenyl-(CH₂)₃-CH(Ar)-COOH]

30. A process according to claim 4, wherein Ar is selected from the following radicals:

[same six heteroaryl radicals as above]

31. A process according to claim 4, wherein Ar is phenyl which optionally can be substituted with up to 3 substituents, and said Knoevenagel condensation with an arylacetic acid of formula X is performed at 100° C.

32. A process according to claim 1, wherein said reagent consists of boron tribromide and 2,6-dimethylpyridine.

33. A process according to claim 13, wherein said reagent consists of boron tribromide and 2,6-dimethylpyridine.

34. A process according to claim 14, wherein said reagent consists of boron tribromide and 2,6-dimethylpyridine.

* * * * *

UNITED STATES PATENT AND TRADEMARK OFFICE
CERTIFICATE OF CORRECTION

PATENT NO.        : 7,321,044 B2                                    Page 1 of 1
APPLICATION NO.   : 10/270080
DATED             : January 22, 2008
INVENTOR(S)       : Johannes Platzek It is certified that error appears in the above-identified patent and that said Letters Patent is hereby corrected as shown below:

Column 22, line 43, reads "Ar a phenyl" should read -- Ar is a phenyl --
Column 22, line 67, reads "an arylacetic acids" should read -- an arylacetic acid --

Signed and Sealed this

Twenty-sixth Day of August, 2008

JON W. DUDAS
*Director of the United States Patent and Trademark Office*